US005441738A

United States Patent [19]

Klein et al.

[11] Patent Number: 5,441,738

[45] Date of Patent: Aug. 15, 1995

[54] PROCESS FOR IMPROVING A GLYCEROLYSED OIL

[75] Inventors: Jean-Marie Klein, Feyzin; Joel Denis, Vourles, both of France

[73] Assignee: Gattefosse SA, France

[21] Appl. No.: 81,355

[22] PCT Filed: Oct. 8, 1992

[86] PCT No.: PCT/FR92/00939

§ 371 Date: Jun. 16, 1993

§ 102(e) Date: Jun. 16, 1993

[87] PCT Pub. No.: WO93/09211

PCT Pub. Date: May 13, 1993

[30] Foreign Application Priority Data

Oct. 31, 1991 [FR] France ................................ 91 13715

[51] Int. Cl.[6] ................................................ A61K 35/78

[52] U.S. Cl. ................................. 424/195.1; 514/783; 426/601

[58] Field of Search ........................ 426/601; 260/428; 424/195.1; 514/783

[56] References Cited

U.S. PATENT DOCUMENTS 3,012,890 12/1961 Dutton et al. .

4,265,826 5/1981 Iida et al. ............................ 260/428

4,272,447 6/1981 Beharry ............................ 260/424

FOREIGN PATENT DOCUMENTS 0041002 12/1981 European Pat. Off. .

0139177 5/1985 European Pat. Off. .

0188015 11/1985 European Pat. Off. .

0262113 10/1989 European Pat. Off. .

0256760 1/1990 European Pat. Off. .

616190 7/1950 United Kingdom .

OTHER PUBLICATIONS

G. Hoffman 'The Chemistry and Technology of Edible Oils and Fats and Their High Fat Products', (1990) Academic Press Chapter 5.

*Primary Examiner*—Douglas W. Robinson

*Assistant Examiner*—Howard C. Lee

*Attorney, Agent, or Firm*—Harris Beach & Wilcox

[57] ABSTRACT

There is disclosed a process for improving a glycerolyzed oil. The oil is heated until any crystals which have formed have disappeared. Then the oil is crystallized by slow stirring for eight to seventy-two hours until an end of crystallization temperature of typically between 0° and 15° is reached. Finally the crystals which have formed are separated at the end of crystallization temperature. The process can be iterated at two successively lower end of crystallization temperatures.

19 Claims, No Drawings

PROCESS FOR IMPROVING A GLYCEROLYSED OIL

BACKGROUND OF THE INVENTION

1. Field of the Invention.

The invention relates to a process for improving a glycerolysed oil; it also relates to the oils thus improved.

2. Description of the Prior Art.

As is known, glycerolysed oils, which are well known as excipients in the pharmaceutical industry, are obtained by glycerolysis in the presence of alkaline catalysts. In one embodiment, these oils contain a residual glycerol level at most equal to one percent (1%).

In the text and the claims, "glycerolysed oil" designates a natural oil of plant or animal origin which has undergone alcoholysis treatment with glycerol, or a direct esterification of its fatty acids on glycerol.

These glycerolysed oils are essentially characterized by the fact that they consist of a mixture of mainly mono- and diesters of glycerol and of a smaller quantity of triesters. These glycerolysed oils must contain at least 90% by weight of glycerides (FDA-21 CFR requirements—Chapter I—§184.1505), and must have a high proportion (at least 50% and in practice of the order of 80%) of unsaturated fatty acids. Oils which may be mentioned are those of plant origin, such as those of corn, sunflower (high and low linoleic acid content) safflower (high and low linoleic acid content), palm (fractionated or otherwise), groundnut or colza, or of animal origin, such as that of tallow.

However, these glycerolysed oils have the bad tendency, when they are stored at room temperature, to crystallize partially and gradually, forming small white crystals which settle after a few hours to several days depending on the thermal history of the samples. These white crystals swell rapidly and render this oil unsuitable for its use as pharmaceutical excipient and partially mask the properties of the active ingredients.

To prevent the formation of these crystals, it has been suggested to add to the oil during the glycerolysis unsaturated fatty acids which form esters which do not precipitate. Unfortunately, this solution is poorly adapted to the pharmaceutical industry since the oil thus treated does not always correspond to the requirements of international standards for the "glycerolysed oil" designation, especially to the requirements of the GRAS (generally recognized as safe) standard based on the FDA (Food and Drug Administration) rules mentioned above.

SUMMARY OF THE INVENTION

The invention overcomes these disadvantages. It relates to a process for improving these glycerolysed oils, and more particularly aims to extract, by a physical process, the portion liable to crystallize, so that the oils thus treated can satisfy the requirements of the pharmaceutical industry.

The invention relates more particularly to a process which makes it possible to obtain a glycerolysed oil which is liquid and clear for at least three days at 15° C., which could not be obtained up until now.

This process for improving a glycerolysed oil is characterized in that it consists:

in heating this oil until the crystals which may have formed disappear;

then in crystallizing this oil with slow stirring for eight to seventy-two hours until an end of crystallization temperature of between 0° and 15° C. is reached;

finally in separating the crystals formed, the procedure being carried out at the same temperature as the end of crystallization temperature.

While this process can be carried out in a single step, it is also possible to use an operation comprising several successive steps. In this case it is important for the characteristic treatment temperature to be lower from one step to the next, and for the temperature of the last step to be between 0° and 15° C.

In a two-stage end of crystallization process, the procedure is advantageously carried out, in a first stage, between 15° and 25° C., and then, in a second stage, between 0° and 15° C.

"End of crystallization temperature" designates the temperature at which the thermal cycle used for the partial crystallization of the product ends, which is in fact carried out over a range of temperatures, and at which the separation stages begin and are carried out.

Advantageously, in practice:

it is essential, in a first stage, to heat in order to remove not only the crystals formed, but also to destroy the thermal history of the oil; it was observed that good results are obtained by heating at 80° C. for one hour;

the passage of the hot glycerolysed oil to the characteristic crystallization stage can be carried out rapidly or better still, slowly, in a gradual manner;

the crystallization is carried out by the so-called "winterization" method, that is to say with slow stirring, so as not to create vortices, in a container by means of a stirrer having the shape of a frame which does not scrape the sides, so as to bring about the appearance of metastable α (alpha) crystals and make possible, by polymorphism, their maturation into larger and stable crystals;

in a first embodiment, the crystallization is carried out by immersing the medium in a bath whose temperature is between the desired thresholds, that is 0° and 15° C. for a single-step operation, and 15°-25° C. then 0°-15° C. for a two-step operation;

in a preferred embodiment, the crystallization is carried out by immersing the medium in a bath whose temperature is programmed to reach the desired thresholds gradually, thereby making it possible to obtain crystals (spherulites) of homogeneous size, which are easily reproducible and easier to separate;

likewise, in the two-step operation, in the second crystallization phase, it is essential to cool to a temperature of at most 15° C. so that the proportion of crystals formed is sufficiently high in order to be able, in this manner, to separate them conveniently; likewise, it is essential that this temperature is lower than the first in order to recover the last crystals which may form, but higher than 0° C. in order to avoid the caking of the entire oil;

in practice, with a glycerolysed corn oil, the best results are obtained by cooling to an end of crystallization temperature of between 8° and 10° C. in order to obtain a longer stability (one or several weeks) when the final product is stored;

the separation of the crystals obtained can be carried out:

either by centrifugation for a period of five to sixty minutes with accelerations of 500 to 12,000 g;

or by filtration on a filter cloth with an opening of 10 to 500 microns, advantageously 50 microns, under a relative pressure of less than five bars, preferably of less than two bars;

or by a combination of these two modes of separation: centrifugation and filtration.

DESCRIPTION OF THE PREFERRED EMBODIMENT

The manner in which the invention can be carried out and the advantages derived therefrom will become more clearly apparent from the exemplary embodiments given below.

EXAMPLE 1

Two liters of a glycerolysed corn oil with a residual glycerol level of less than one percent (1%), sold by the Applicant under the name MAISINE, are used. This oil contains 37.0% (by mass) of monoglycerides, 48.0% of diglycerides and 14.5% of triglycerides, and the remainder as glycerol and free fatty acids. The fatty acids which make up these glycerides represent 10.1% of $C_{16}$ fatty acid (palmitic acid), 2.6% of $C_{18}$ (stearic acid), 29.6% of $C_{18:1}$ (oleic acid), 54.2% of $C_{18:2}$ (linoleic acid), 1.1% of $C_{18:3}$ (linolenic acid), the remainder as higher fatty acids.

When this glycerolysed oil is stored at room temperature, a substantial quantity of white crystals is formed which settle at the bottom and then swell very rapidly until spherulites of widely varying diameters of between 10 and 500 microns are formed which are very difficult to separate. After three days, this glycerolysed oil is partially caked.

EXAMPLE 2

This glycerolysed oil is then heated in an oven for one hour at 80° C. until the crystals formed completely disappear, but also until the thermal history of this sample disappears.

The hot glycerolysed oil is then placed in a three-liter beaker surrounded by a bath thermostated at 20° C. It is stirred slowly by means of a frame made up of three vertical bars five centimeters apart, connected to each other by two horizontal bars ten centimeters apart. The speed of rotation of this winterization stirrer is 25 revolutions/minute. The stirring is thus carried out at 20° C. for forty-eight hours.

The pasty liquid obtained is then transferred into six 300-ml centrifuge bowls and the centrifugation is carried out at this same temperature of 20° C. for ten minutes at 4,000 revolutions/minute, that is to say at 3,500 g.

The supernatant liquid phase is extracted by decantation and this liquid phase is recovered. The remaining pellet sticks to the sides. A yield of liquid phase of about 50% is obtained.

This liquid phase is again heated at 80° C. for one hour, then crystallized at 5° C. (end of crystallization temperature) for forty-eight hours by means of the same equipment, and then centrifuged again at this temperature of 5° C. for ten minutes at 3,500 g.

A new liquid phase is extracted (yield of 70% that is to say a total yield of 35%).

The fractionated glycerolysed oil obtained contains:

| | |
|---|---|
| 34.2% of monoglycerides | (against 37.0%), |
| 50.1% of diglycerides | (against 48.0%), |
| 15.3% of triglycerides | (against 14.5%). |

The fatty acids which make up these glycerides represent:

| | |
|---|---|
| 8.1% of $C_{16}$ | (against 10.1%), |
| 2.0% of $C_{18}$ | (against 2.6%), |
| 30.4% of $C_{18:1}$ | (against 29.6%), |
| 56.4% of $C_{18:2}$ | (against 54.2%), |
| 1.2% of $C_{18:3}$ | (against 1.1%). |

A drop of two points in the proportion of $C_{16}$ is therefore observed which favors the desired tendency to crystallize less.

The fractionated glycerolysed oil obtained is perfectly clear at 15° C. for at least four days and satisfies the legal definition of glycerolysed corn oil. It is completely inert towards active ingredients and the medication of the excipient compound supplemented with the active ingredient remains constant over time in a given volume since this medication is not affected by the appearance of unwanted crystals, which could not be achieved up until now.

The glycerolysed oil thus treated facilitates the lyoavailability of the active ingredients per os. As already stated, this oil is perfectly suitable as excipient for a medicinal product intended to be administered orally.

EXAMPLE 3

Example 1 is repeated but replacing the two separation-centrifugation stages by two filtration stages through a screen with a mesh of 50 microns, under a relative pressure of 0.5 bars.

An oil which is clear at room temperature is obtained containing:

| | |
|---|---|
| 32.1% of monoglycerides | (against 37.0%), |
| 52.1% of diglycerides | (against 48.0%), |
| 15.5% of triglycerides | (against 14.5%). |

The fatty acids which make up these saturated monoglyceride-depleted glycerides represent 7.8% of (against 10.1%).

The decrease in the proportion of $C_{16}$, linked to the depletion of saturated monoglycerides, favors the desired reduction in the tendency to crystallize.

EXAMPLE 4

Example 1 is repeated by replacing the glycerolysed corn oil by glycerolysed sunflower oil, which has a free glycerol level of less than 2.5%.

Comparable results are obtained.

EXAMPLE 5

50 kilograms of a glycerolysed oil having the specifications below are loaded into a crystallizing dish with a capacity of about one hundred liters, equipped with a rotating paddle mixer and cooled by a coil, immersed in the said oil, in which a liquid coolant circulates.

The glycerolysed corn oil contains 37.0% (by mass) of monoglycerides; 47.7% of diglycerides and 14.7% of triglycerides and the remainder as glycerol and free fatty acids. The fatty acids which make up these glycerides represent 10.5% of $C_{16}$ fatty acid (palmitic acid); 2.1% of $C_{18:2}$ (stearic acid); 29.1% of $C_{18:1}$ (oleic acid); 54.7% of $C_{18:2}$ (linoleic acid); 1.0% of $C_{18:3}$ (linolenic acid); the remainder as higher fatty acids.

These fatty acids are randomly distributed in the glyceride mixture. The fatty acid compositions of the glyceride fractions are as follows:

| | |
|---|---|
| In the monoglycerides: | 12.5% of $C_{16}$ |
| | 2.2% of $C_{18}$ |
| | 28.9% of $C_{18:1}$ |
| | 55.1% of $C_{18:2}$ |
| | 0.8% of $C_{18:3}$ |
| In the diglycerides: | 12.5% of $C_{16}$ |
| | 2.2% of $C_{18}$ |
| | 28.4% of $C_{18:1}$ |
| | 55.4% of $C_{18:2}$ |
| | 0.9% of $C_{18:3}$ |
| In the triglycerides: | 13.6% of $C_{16}$ |
| | 2.7% of $C_{18}$ |
| | 29.2% of $C_{18:1}$ |
| | 52.9% of $C_{18:2}$ |
| | 0.8 % of $C_{18:3}$. |

In these glyceride fractions, the remainder consists of higher fatty acids.

The characteristic values for this glycerolysed corn oil are as follows:

Acid value=0.3
Saponification value=167
Hydroxyl value=168
Peroxide value =0.8
Iodine value=111.2.

Stored at room temperature, a high quantity of white crystals mainly consisting of glycerides saturated especially with glycerol monopalmitate, is formed in this glyerolysed oil. Two days after storage, the glycerolysed oil is cloudy and two weeks after storage at room temperature, the glycerolysed oil is partially caked and a substantial white deposit is situated at the bottom of the barrel, which makes it difficult to use.

This glycerolysed oil is heated at 80° C. for about thirty minutes in order to destroy its thermal history, and it is then gradually cooled stepwise by constantly adjusting the difference in temperature between the oil and the liquid coolant.

In a first stage, the cooling is carried out over six hours down to 26° C. by adjusting the stirring to 30 revolutions/minute. At any instant, the coolant has a temperature three degrees (3° C.) below that of the oil.

The oil is then cooled from 26° C. to 19° C. over 13 hours, still with stirring but adjusted to 15 revolutions/minute, and the temperature of the coolant is one degree (1° C.) below that of the oil.

It is then cooled from 19° to 8° C., still with the stirring adjusted to 15 revolutions/minute, over 11 hours, but constantly adjusting the difference in temperature between that of the coolant and that of the oil to three degrees (3° C.).

In the rest of the operation, the oil is maintained at the end of crystallization temperature of eight degrees (8° C.).

When the glycerolysed oil is examined under a microscope, it is observed that the solid phase consists of spherulites of a mean diameter of 350 microns, immersed in a liquid phase. It is filtered on a membrane filter press placed in a cold chamber in order to separate the spherulites from the oil which it is desired to recover. This separation is facilitated by the homogeneous diameter of these spherulites. The filter is supplied by a variable capacity pump adjusted so that the supply pressure is at about 2 relative bars.

After filtration, the cake of the crystallized phase obtained is compressed at 4 bars in order to expel the excess oil.

A perfectly clear liquid phase (fractionated glycerolysed oil) is obtained which has the following characteristics:

| | |
|---|---|
| 30.9% of monoglycerides start, | (against 37.0%) at the |
| 52.3% of diglycerides | (against 47.7%) |
| 16.3% of triglycerides | (against 14.7%). |
| Constituent fatty acids: | |
| 7.8% of $C_{16}$ | (against 10.5%), |
| 1.5% of $C_{18}$ | (against 2.1%), |
| 28.9% of $C_{18:1}$ | (against 29.1%), |
| 58.2% of $C_{18:2}$ | (against 54.7%), |

Composition of fatty acids in the glyceride fractions:

| | |
|---|---|
| In the monoglycerides: | |
| 3.2% of $C_{16}$ | (against 12.5%), |
| 0.6% of $C_{18}$ | (against 2.2%), |
| 29.8% of $C_{18:1}$ | (against 28.9%), |
| 64.4% of $C_{18:2}$ | (against 55.1%). |
| In the diglycerides: | |
| 10.2% of $C_{16}$ | (against 12.5%), |
| 1.9% of $C_{18}$ | (against 2.2%), |
| 29.1% of $C_{18:1}$ | (against 28.4%), |
| 56.8% of $C_{18:2}$ | (against 55.4%). |
| In the triglycerides: | |
| 11.2% of $C_{16}$ | (against 13.6%), |
| 2.2% of $C_{18}$ | (dgainst 2.7%), |
| 28.9% of $C_{18:1}$ | (dgdinst 29.2%), |
| 56.2% of $C_{18:2}$ | (against 52.9%). |

The characteristic values for this fractionated glycerolysed corn oil are as follows:

| | |
|---|---|
| Acid value = 0.5 | (against 0.3) |
| Iodine value = 117.4 | (against 111.2) |
| Saponification value = 175 | (against 167) |
| Peroxide value = 6.0 | (against 0.8). |

We claim:

1. A process of preparing a fractionated glycerolyzed oil having improved crystallization stability, consisting essentially of the steps of:

heating the glycerolyzed oil to a temperature of about 80° C. and maintaining the glycerolyzed oil at said temperature until crystals are absent therein, the glycerolyzed oil being richer in monoglycerides and diglycerides than in triglycerides;

cystallizing the heated glycerolyzed oil by simultaneously cooling and slowly stirring for a period of about eight to seventy-two hours until a first end of crystallization temperature of between about 0° and 25° C. is reached; and removing crystals from the crystallized oil at said first end of crystallization temperature.

2. The process according to claim 1, wherein said oil is a corn oil, and said first end of crystallization temperature is between 8° and 10° C.

3. A glycerolyzed oil produced by the process of claim 1.

4. The process according to claim 1, wherein said step of heating and maintaining is performed for one hour and said elevated temperature is 80° C.

5. The process according to claim 1, wherein said step of crystallizing is performed in a container having sides using a stirrer that stirs the oil without contacting said sides and without creating vortices therein.

6. The process according to claim 1, wherein said step of removing crystals is performed by centrifuging at a temperature exceeding 0° C. and not exceeding 15° C. for a period of five to sixty minutes at an acceleration of 500 to 12,000 g.

7. The process according to claim 1, wherein said step of removing crystals at said first end of crystallization temperature crystals at said second end of crystallization temperature is performed by filtering at a temperature of between 0° C. and 15° C. through a filter cloth having an opening of 10 to 500 microns under a relative pressure of less than five bars.

8. The process according to claim 1, wherein said step of removing crystals at said first end of crystallization temperature crystals at said second end of crystallization temperature is performed by filtering at a temperature of between 0° C. and 15° C. through a filter cloth having an opening of 10 to 500 microns under a relative pressure of less than five bars, and by centrifuging at a temperature exceeding 0° C. and not exceeding 15° C. for a period of five to sixty minutes at an acceleration of 500 to 12,000 g.

9. The process according to claim 1, wherein said first end of crystallization temperature is between about 15° and 25° C., said step of removing crystals yields a partially decrystallized oil, the process further consisting essentially of the steps of:

heating the partially decrystallized oil until residual crystals therein are dissolved;

crystallizing the heated partially decrystallized oil by simultaneously cooling and slowly stirring for a period of about eight to seventy-two hours until a second temperature of between about 0° and 15° C. is reached; and removing crystals from the cooled partially decrystallized oil at said second temperature.

10. The process according to claim 9, wherein said step of crystallizing the heated oil and said step of crystallizing the heated partially decrystallized oil are performed in a container having sides using a stirrer that stirs the oil without contacting said sides and without creating vortices therein.

11. The process according to claim 9, wherein said step of heating and maintaining is performed for one hour and said elevated temperature is 80° C., and said step of heating the partially decrystallized oil is performed for one hour at 80° C.

12. The process according to claim 9, wherein said step of removing crystals at said first end of crystallization temperature and said step of removing crystals at said second temperature are each performed by centrifuging at a temperature exceeding 0° C. and not exceeding 15° C. for a period of five to sixty minutes at an acceleration of 500 to 12,000 g.

13. The process according to claim 9, wherein said step of removing crystals at said first end of crystallization temperature and said step of removing crystals at said second temperature are each performed by filtering at a temperature of between 0° C. and 15° C. through a filter cloth having an opening of 10 to 500 microns under a relative pressure of less than five bars.

14. The process according to claim 9, wherein said step of removing crystals at said first end of crystallization temperature and said step of removing crystals at said second temperature are each performed by filtering at a temperature of between 0° C. and 15° C. through a filter cloth having an opening of 10 to 500 microns under a relative pressure of less than five bars, and centrifuging at a temperature exceeding 0° C. and not exceeding 15° C. for a period of five to sixty minutes at an acceleration of 500 to 12,000 g.

15. A process of preparing a fractionated glycerolyzed oil having improved crystallization stability, consisting essentially of the steps of:

heating the glycerolyzed oil and maintaining the glycerolyzed oil for one hour at 80° C.;

crystallizing the heated glycerolyzed oil by simultaneously cooling and stirring the glycerolyzed oil without contacting the side of the container and without creating vortices therein for a period of about eight to seventy-two hours until a first end of crystallization temperature of between about 0° and 25° C. is reached, said step of crystallizing the heated glycerolyzed oil being performed without seeding the glycerolyzed oil and in an absence of alkalinizing reagents;

removing crystals from the crystallized oil by centrifuging at a temperature exceeding 0° C. and not exceeding 15° C. for a period of five to sixty minutes at an acceleration of 500 to 12,000 g to yield a partially decrystallized oil;

heating the partially decrystallized oil for one hour at 80° C.;

crystallizing the heated partially decrystallized oil by simultaneously cooling and slowly stirring for a period of about eight to seventy-two hours until a second temperature of between about 0° and 15° C. is reached; and removing crystals from the cooled partially decrystallized oil by centrifuging at a temperature exceeding 0° C. and not exceeding 15° C. for a period of five to sixty minutes at an acceleration of 500 to 12,000 g; whereby a fractionated glycerolyzed oil having improved crystallization stability is obtained.

16. The process according to claim 15, wherein said oil is a corn oil, and said first end of crystallization temperature is between 8° and 10° C.

17. The process according to claim 15, wherein said step of removing crystals from the crystallized oil and said step of removing crystals from the cooled partially decrystallized oil each further comprise the step of filtering the oil at a temperature of between 0° C. and 15° C. through a filter cloth having an opening of 10 to 500 microns under a relative pressure of less than five bars.

18. The process according to claim 17, wherein said oil is a corn oil, and said first end of crystallization temperature is between 8° and 10° C.

19. The process according to claim 16, wherein said step of removing crystals from the cooled partially decrystallized oil is performed without seeding the oil and in an absence of alkalinizing reagents.

* * * * *